(12) United States Patent
Lulla et al.

(10) Patent No.: US 8,933,060 B2
(45) Date of Patent: *Jan. 13, 2015

(54) COMBINATION OF AZELASTINE AND CICLESONIDE FOR NASAL ADMINISTRATION

(71) Applicant: Cipla House, Mumbai (IN)

(72) Inventors: Amar Lulla, Mumbai (IN); Geena Malhotra, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/644,126

(22) Filed: Oct. 3, 2012

(65) Prior Publication Data

US 2013/0029951 A1 Jan. 31, 2013

Related U.S. Application Data

(60) Continuation of application No. 12/508,393, filed on Jul. 23, 2009, now Pat. No. 8,304,405, which is a division of application No. 10/518,016, filed as application No. PCT/GB03/02557 on Jun. 13, 2003, now Pat. No. 8,168,620.

(30) Foreign Application Priority Data

Jun. 14, 2002 (GB) .................................. 0213739.6

(51) Int. Cl.
*A01N 45/00* (2006.01)
*A61K 31/55* (2006.01)
*A61K 31/58* (2006.01)
*A61K 31/573* (2006.01)

(52) U.S. Cl.
CPC ............... *A61K 31/573* (2013.01); *A61K 31/55* (2013.01); *A61K 31/58* (2013.01)
USPC ....................................................... 514/171

(58) Field of Classification Search
None
See application file for complete search history.

(56) References Cited

U.S. PATENT DOCUMENTS

| | | | |
|---|---|---|---|
| 2,837,464 A | 6/1958 | Nobile | |
| 3,067,197 A | 12/1962 | Agnello et al. | |
| 3,312,590 A | 4/1967 | Elks et al. | |
| 3,506,694 A | 4/1970 | Oxley | |
| 3,557,162 A | 1/1971 | Lens et al. | |
| 3,639,434 A | 2/1972 | Oxley et al. | |
| 3,755,302 A | 8/1973 | Ercoli et al. | |
| 3,813,384 A | 5/1974 | Vogelsang et al. | |
| 3,828,080 A | 8/1974 | Phillipps et al. | |
| 3,856,828 A | 12/1974 | Phillipps et al. | |
| 3,891,631 A | 6/1975 | Phillipps et al. | |
| 3,981,894 A | 9/1976 | Phillipps et al. | |
| 3,989,686 A | 11/1976 | Phillipps et al. | |
| 4,093,721 A | 6/1978 | Phillipps et al. | |
| 4,113,680 A | 9/1978 | Kamano et al. | |
| 4,187,301 A | 2/1980 | Edwards | |
| 4,188,385 A | 2/1980 | Edwards | |
| 4,198,403 A | 4/1980 | Alvarez | |
| 4,221,787 A | 9/1980 | Bodor et al. | |
| 4,261,984 A | 4/1981 | Alvarez | |
| 4,263,289 A | 4/1981 | Edwards | |
| 4,267,173 A | 5/1981 | Draper | |
| 4,285,937 A | 8/1981 | Kalvoda | |
| 4,310,466 A | 1/1982 | Edwards | |
| 4,335,121 A | 6/1982 | Phillipps et al. | |
| 4,377,575 A | 3/1983 | Stache et al. | |
| 4,472,393 A | 9/1984 | Shapiro | |
| 4,607,028 A | 8/1986 | Schmidlin | |
| 4,710,495 A | 12/1987 | Bodor | |
| 4,861,765 A | 8/1989 | Mitsukuchi et al. | |
| 4,992,474 A | 2/1991 | Skidmore et al. | |
| 4,994,439 A | 2/1991 | Longenecker et al. | |
| 4,996,335 A | 2/1991 | Bodor | |
| 5,063,222 A | 11/1991 | Komoto et al. | |
| 5,081,113 A | 1/1992 | Claussner et al. | |
| 5,086,050 A | 2/1992 | Hettche et al. | |
| 5,164,194 A | 11/1992 | Hettche | |
| 5,202,316 A | 4/1993 | Claussner et al. | |
| 5,232,919 A | 8/1993 | Scheffler et al. | |
| 5,271,946 A | 12/1993 | Hettche | |
| 5,362,721 A | 11/1994 | Stache et al. | |
| 5,420,120 A | 5/1995 | Boltralik | |

(Continued)

FOREIGN PATENT DOCUMENTS

| | | | |
|---|---|---|---|
| AU | 2003244799 B2 | 12/2003 | |
| BE | 889563 A1 | 11/1981 | |
| DE | 1059906 B | 6/1959 | |
| DE | 2164058 A1 | 7/1972 | |
| DE | 3836579 A1 | 5/1989 | |

(Continued)

OTHER PUBLICATIONS

Di Lorenzo, G., et al., "Randomized placebo-controlled trial comparing fluticasone aqueous nasal spray in mono-therapy, fluticasone plus cetirizine, fluticasone plus montelukast and cetirizine plus montelukast for seasonal allergic rhinitis," Clinical and Experimental Allergy, 2004, vol. 34, pp. 259-267, Blackwell Publishing Ltd.

(Continued)

*Primary Examiner* — Sue Liu
*Assistant Examiner* — Thor Nielsen
(74) *Attorney, Agent, or Firm* — Conley Rose, P.C.; Rodney B. Carroll

(57) ABSTRACT

A pharmaceutical product or formulation, which comprises azelastine or a pharmaceutically acceptable salt, solvate or physiologically functional derivative thereof, and a steroid, or a pharmaceutical acceptable salt, solvate or physiologically functional derivative thereof, preferably the product or formulation being in a form suitable for nasal or ocular administration.

26 Claims, No Drawings

(56) References Cited

U.S. PATENT DOCUMENTS

| | | |
|---|---|---|
| 5,608,093 A | 3/1997 | Stache et al. |
| 5,658,549 A | 8/1997 | Akehurst et al. |
| 5,658,919 A | 8/1997 | Ratnaraj et al. |
| 5,707,984 A | 1/1998 | Tjoeng et al. |
| 5,830,490 A | 11/1998 | Weinstein et al. |
| 5,837,699 A | 11/1998 | Sequeira et al. |
| 5,849,265 A | 12/1998 | Li-Bovet et al. |
| 5,889,015 A | 3/1999 | Sequeira et al. |
| 5,914,122 A | 6/1999 | Otterbeck et al. |
| 5,972,920 A | 10/1999 | Seidel |
| 5,981,517 A | 11/1999 | Bodor |
| 6,017,963 A | 1/2000 | Alfonso et al. |
| 6,057,307 A | 5/2000 | Sequeira et al. |
| 6,127,353 A | 10/2000 | Yuen et al. |
| 6,136,294 A | 10/2000 | Adjei et al. |
| 6,197,761 B1 | 3/2001 | Biggadike et al. |
| 6,241,969 B1 | 6/2001 | Saidi et al. |
| 6,261,539 B1 | 7/2001 | Adjei et al. |
| 6,294,153 B1 | 9/2001 | Modi |
| 6,319,513 B1 | 11/2001 | Dobrozsi |
| 6,330,938 B1 | 12/2001 | Hērvée et al. |
| 6,391,340 B1 | 5/2002 | Malmqvist-Granlund et al. |
| 6,395,300 B1 | 5/2002 | Straub et al. |
| 6,416,743 B1 | 7/2002 | Fassberg et al. |
| 6,537,983 B1 | 3/2003 | Biggadike et al. |
| 6,583,180 B2 | 6/2003 | Link et al. |
| 6,750,210 B2 | 6/2004 | Biggadike |
| 6,759,398 B2 | 7/2004 | Biggadike |
| 6,777,399 B2 | 8/2004 | Biggadike et al. |
| 6,777,400 B2 | 8/2004 | Biggadike et al. |
| 6,787,532 B2 | 9/2004 | Biggadike et al. |
| 6,835,724 B2 | 12/2004 | Stache et al. |
| 6,858,593 B2 | 2/2005 | Biggadike et al. |
| 6,858,596 B2 | 2/2005 | Biggadike et al. |
| 6,878,698 B2 | 4/2005 | Biggadike et al. |
| 6,921,757 B2 | 7/2005 | Cuenoud et al. |
| 7,101,866 B2 | 9/2006 | Biggadike et al. |
| 7,125,985 B2 | 10/2006 | Biggadike et al. |
| 7,132,532 B2 | 11/2006 | Biggadike et al. |
| 7,144,845 B2 | 12/2006 | Biggadike et al. |
| 7,214,672 B2 | 5/2007 | Komoto et al. |
| 7,244,742 B2 | 7/2007 | Pieper et al. |
| 7,288,536 B2 | 10/2007 | Biggadike et al. |
| 7,291,608 B2 | 11/2007 | Biggadike et al. |
| 7,291,609 B2 | 11/2007 | Biggadike et al. |
| 7,405,206 B2 | 7/2008 | Biggadike et al. |
| 7,498,321 B2 | 3/2009 | Biggadike et al. |
| 7,524,970 B2 | 4/2009 | John |
| 7,531,528 B2 | 5/2009 | Biggadike et al. |
| 7,541,350 B2 | 6/2009 | Biggadike et al. |
| 7,579,335 B2 | 8/2009 | Biggadike et al. |
| 7,592,329 B2 | 9/2009 | Biggadike et al. |
| 7,629,335 B2 | 12/2009 | Biggadike et al. |
| 7,638,508 B2 | 12/2009 | Biggadike et al. |
| 7,776,315 B2 | 8/2010 | Pairet et al. |
| 8,071,073 B2 | 12/2011 | Dang et al. |
| 8,163,723 B2 | 4/2012 | Lulla et al. |
| 8,168,620 B2 | 5/2012 | Lulla et al. |
| 2002/0061281 A1 | 5/2002 | Osbakken et al. |
| 2002/0076382 A1 | 6/2002 | Kaplan et al. |
| 2002/0081266 A1 | 6/2002 | Woolfe et al. |
| 2003/0018019 A1 | 1/2003 | Meade et al. |
| 2004/0136918 A1 | 7/2004 | Garrett et al. |
| 2004/0204399 A1 | 10/2004 | Osbakken et al. |
| 2004/0235807 A1 | 11/2004 | Weinrich et al. |
| 2004/0242638 A1 | 12/2004 | Yanni et al. |
| 2005/0163724 A1 | 7/2005 | Miyadai et al. |
| 2005/0192261 A1 | 9/2005 | Jost-Price et al. |
| 2006/0002861 A1 | 1/2006 | Biggadike |
| 2006/0228306 A1 | 10/2006 | Lane |
| 2007/0020330 A1 | 1/2007 | Dang et al. |
| 2009/0124585 A1 | 5/2009 | Cross et al. |
| 2009/0156567 A1 | 6/2009 | Biggadike |
| 2009/0286762 A1 | 11/2009 | Myles et al. |
| 2010/0152147 A1 | 6/2010 | Fuge et al. |
| 2010/0311706 A1 | 12/2010 | Biggadike et al. |
| 2012/0065177 A1 | 3/2012 | Myles et al. |
| 2013/0029952 A1 | 1/2013 | Lulla et al. |

FOREIGN PATENT DOCUMENTS

| | | |
|---|---|---|
| DE | 19947234 A1 | 4/2001 |
| DE | 10152369 A1 | 5/2002 |
| EP | 0004773 A2 | 10/1979 |
| EP | 0057401 A1 | 8/1982 |
| EP | 0179583 A1 | 4/1986 |
| EP | 0393658 B1 | 10/1990 |
| EP | 0416951 A1 | 3/1991 |
| EP | 0780127 A1 | 6/1997 |
| EP | 1519731 B1 | 4/2009 |
| EP | 2072051 A1 | 6/2009 |
| GB | 1191965 | 5/1970 |
| GB | 1296458 | 11/1972 |
| GB | 1384372 | 2/1975 |
| GB | 1438940 | 6/1976 |
| GB | 1517278 | 7/1978 |
| GB | 2079755 A | 1/1982 |
| GB | 2088877 A | 6/1982 |
| GB | 2140800 A | 12/1984 |
| GB | 2389530 A | 12/2003 |
| IL | 109656 A | 2/1998 |
| JP | 4208267 A | 7/1992 |
| JP | 8291072 A | 11/1996 |
| JP | 8291073 A | 11/1996 |
| JP | 200253485 A | 2/2002 |
| WO | 8504589 A1 | 10/1985 |
| WO | 8903390 A1 | 4/1989 |
| WO | 9015816 A1 | 12/1990 |
| WO | 9104252 A1 | 4/1991 |
| WO | 9214472 A1 | 9/1992 |
| WO | 9531964 A1 | 11/1995 |
| WO | 9619199 A1 | 6/1996 |
| WO | 9632151 A1 | 10/1996 |
| WO | 9701337 A1 | 1/1997 |
| WO | 9705136 A1 | 2/1997 |
| WO | 9715298 A1 | 5/1997 |
| WO | 9721721 A1 | 6/1997 |
| WO | 9721724 A1 | 6/1997 |
| WO | 9724365 A1 | 7/1997 |
| WO | 9740836 A1 | 11/1997 |
| WO | 9746243 A1 | 12/1997 |
| WO | 9817676 A1 | 4/1998 |
| WO | 9834596 A2 | 8/1998 |
| WO | 9848839 A1 | 11/1998 |
| WO | 9901467 A2 | 1/1999 |
| WO | 9925359 A1 | 5/1999 |
| WO | 9932089 A1 | 7/1999 |
| WO | 0016814 A1 | 3/2000 |
| WO | 0033892 A1 | 6/2000 |
| WO | 0038811 A1 | 7/2000 |
| WO | 0048587 A1 | 8/2000 |
| WO | 0049993 A2 | 8/2000 |
| WO | 0066522 A1 | 11/2000 |
| WO | 0104118 A2 | 1/2001 |
| WO | 0120331 A1 | 3/2001 |
| WO | 0154481 A2 | 8/2001 |
| WO | 0154664 A1 | 8/2001 |
| WO | 0157025 A1 | 8/2001 |
| WO | 0162722 A2 | 8/2001 |
| WO | 0178736 A1 | 10/2001 |
| WO | 0178739 A1 | 10/2001 |
| WO | 0178741 A1 | 10/2001 |
| WO | 0178745 A1 | 10/2001 |
| WO | 0200199 A1 | 1/2002 |
| WO | 0200679 A2 | 1/2002 |
| WO | 0202565 A2 | 1/2002 |
| WO | 0207767 A2 | 1/2002 |
| WO | 0208243 A1 | 1/2002 |
| WO | 0211711 A2 | 2/2002 |
| WO | 0212265 A1 | 2/2002 |
| WO | 0212266 A1 | 2/2002 |
| WO | 0213868 A1 | 2/2002 |
| WO | 0226723 A1 | 4/2002 |
| WO | 0236106 A2 | 5/2002 |

(56) References Cited

FOREIGN PATENT DOCUMENTS

| WO | 02051422 A1 | 7/2002 |
|----|-------------|--------|
| WO | 02053186 A2 | 7/2002 |
| WO | 02066422 A1 | 8/2002 |
| WO | 02070490 A1 | 9/2002 |
| WO | 02076933 A1 | 10/2002 |
| WO | 02085296 A2 | 10/2002 |
| WO | 02088167 A1 | 11/2002 |
| WO | 02100879 A1 | 12/2002 |
| WO | 03000241 A2 | 1/2003 |
| WO | 03013427 A2 | 2/2003 |
| WO | 03033000 A1 | 4/2003 |
| WO | 03035668 A2 | 5/2003 |
| WO | 03040691 A2 | 5/2003 |
| WO | 03042229 A1 | 5/2003 |
| WO | 03042230 A1 | 5/2003 |
| WO | 03048181 A1 | 6/2003 |
| WO | 03062259 A2 | 7/2003 |
| WO | 03064445 A1 | 8/2003 |
| WO | 03066033 A1 | 8/2003 |
| WO | 03066036 A1 | 8/2003 |
| WO | 03066656 A1 | 8/2003 |
| WO | 03072592 A1 | 9/2003 |
| WO | 03086399 A1 | 10/2003 |
| WO | 03105856 A1 | 12/2003 |
| WO | 2004013156 A1 | 2/2004 |
| WO | 2004019955 A1 | 3/2004 |
| WO | 2005005451 A1 | 1/2005 |
| WO | 2005005452 A1 | 1/2005 |
| WO | 2006058022 A1 | 6/2006 |
| WO | 2007061454 A1 | 5/2007 |
| WO | 2008012338 A2 | 1/2008 |
| WO | 2008012338 A3 | 1/2008 |
| ZA | 872389 | 4/1987 |

OTHER PUBLICATIONS

Dolovich, Jerry, et al., "Multicenter trial of fluticasone propionate aqueous nasal spray in ragweed allergic rhinitis," Annals of Allergy, Aug. 1994, vol. 73, pp. 147-153.

Drouin, Michel A., et al., "Adding Loratadine to Topical Nasal Steroid Therapy Improves Moderately Severe Seasonal Allergic Rhinoconjunctivitis," Advances in Therapy, vol. 12, No. 6, Nov./Dec. 1995, pp. 340-349, Health Communications Inc.

Duonase Data Sheet, "The Complete Rhinitis Control," 6 pages, Cipla Limited, Mumbai, India, 2012.

Dykewicz, Mark S., et al., "Diagnosis and Management of Rhinitis: Complete Guidelines of the Joint Task Force on Practice Parameters in Allergy, Asthma and Immunology," Annals of Allergy, Asthma, & Immunology, vol. 81, Nov. (Part II) 1998, pp. 478-518.

File history of Australian Patent Application No. AU2003244799, 38 pages, 2012.

File history of Brazilian Patent Application No. PI 0312128-3, 27 pages, 2012.

File history of Canadian Patent Application No. 2,489,427, 19 pages, 2012.

File history of Korean Patent Application No. 10-2004-7020819, 89 pages, 2012.

File history of Mexican Patent Application No. Pa/a/2004/01266 (now Patent No. 265349), 86 pages, 2012.

File history of Polish Patent Application No. P-373001, 95 pages, 2012.

File history of Russian Patent Application No. RU 2361593 C2, 65 pages, 2012.

File history of South African Patent Application No. 2005/0331 (now Patent No. 2005/0331), 18 pages.

Fluticasone Furoate, STN Registry No. 397864-44-7, Entered STN: Mar. 4, 2002, p. 1, © 2010 ACS on STN.

Foreign communication from a related counterpart application—Australian Application No. 2003244799, Examination Report, Nov. 20, 2007, 2 pages.

Foreign communication from a related counterpart application—Canadian Application No. 2,489,427, Examination Report, Jun. 18, 2010, 3 pages.

Foreign communication from a related counterpart application—Canadian Application No. 2,489,427, Examination Report, Mar. 24, 2011, 2 pages.

Foreign communication from a related counterpart application—Examination Report, European Application No. 03738280.1, Jul. 18, 2007, 5 pages.

Foreign communication from a related counterpart application—Examination Report, European Application No. 03738280.1, Nov. 10, 2005, 4 pages.

Foreign communication from a related counterpart application—European Application No. 03738280.1, Notice of Intent to Grant, Oct. 23, 2008, 6 pages.

Foreign communication from a related counterpart application—Examination Report, Russian Application No. 2005100781, Apr. 23, 2007, 6 pages.

Foreign communication from a related counterpart application—Examination Report, Russian Application No. 2005100781, May 23, 2008, 3 pages.

Foreign communication from a related counterpart application—Korean Application No. 10-2004-7020819, Examination Report, Aug. 26, 2010, 8 pages.

Foreign communication from a related counterpart application—Notice of Opposition, European Application No. 03738280.1, Feb. 22, 2010, 22 pages.

Foreign communication from a related counterpart application—Summons to Attend Oral Proceedings, European Application No. 03738280.1, Feb. 8, 2011, 1 page.

Foreign communication from a related counterpart application—Translation of Office Action, Israeli Patent Application No. 165771, Jul. 11, 2011, 3 pages.

Foreign communication from the priority application—International Preliminary Examination Report, PCT/GB03/02557, Aug. 26, 2004, 6 pages.

Foreign communication from the priority application—International Search Report, PCT/GB03/02557, Sep. 17, 2003, 3 pages.

Foreign communication from the priority application—Search Report, Great Britain Application No. 0213739.6, Nov. 22, 2002, 4 pages.

Foreign communication from a related counterpart application—First Examination Report, Indian Application No. 1696/MUMNP/2009, Jun. 27, 2012, 2 pages.

Foreign communication from a related counterpart application—First Examination Report, Indian Application No. 1695/MUMNP/2009, Jun. 29, 2012, 2 pages.

Foreign communication from a related counterpart application—Final Office Action, Korean Application No. 10-2011-7022532, Aug. 24, 2012, 6 pages.

Foreign communication from a related counterpart application—Final Office Action, Korean Application No. 10-2011-7022533, Aug. 24, 2012, 6 pages.

Foreign communication from a related counterpart application—Office Action, European Application No. 09075100.9, Aug. 8, 2012, 6 pages.

Foreign communication from a related counterpart application—EPO Communication, European Application No. 09075101.7, Aug. 8, 2012, 5 pages.

Fowler, Stephen J., et al., "Step-down therapy with low-dose fluticasone-salmeterol combination or medium-dose hydrofluoroalkane 134a-beclomethasone alone," J Allergy Clin Immunol, vol. 109, No. 6, Jun. 2002, pp. 929-935, Mosby, Inc.

Galant, Stanley P., et al., "Clinical Prescribing of Allergic Rhinitis Medication in the Preschool and Young School-Age Child; What are the Options?," BioDrugs, 2001, vol. 15, No. 7, pp. 453-463, ADIS International Limited.

Garner, R. C., et al., "A validation study comparing accelerator MS and liquid scintillation counting for analysis of 14C-labelled drugs in plasma, urine and faecal extracts," Journal of Pharmaceutical and Biomedical Analysis, vol. 24, 2000, pp. 197-209, Elsevier Science B.V.

Gawchik, Sandra M., et al., "Comparison of intranasal triamcinolone acetonide with oral loratadine in the treatment of seasonal ragweed-induced allergic rhinitis," The American Journal of Managed Care, Jul. 1997, vol. 3, No. 7, pp. 1052-1058.

(56) References Cited

OTHER PUBLICATIONS

Gennaro, Alfonso R., et al., Remington: The Science and Practice of Pharmacy, 2000, 20th edition, vol. 1, pp. 785, 830, 831 plus cover page and publication pages, Lippincott Williams & Wilkins, a Walters Kluwer Company.
Gilbert, Peter, et al., "Preservation of Pharmaceutical Products," Encyclopedia of Pharmaceutical Technology, 2002, 2nd edition, vol. 3, p. 2278 plus cover page and publication pages, Marcel Dekker, Inc.
Hampel, Frank C., et al., "Double-blind, placebo-controlled study of azelastine and fluticasone in a single nasal spray delivery device," Annals of Allergy, Asthma & Immunology, vol. 105, pp. 168-173, Aug. 2010, American College of Allergy, Asthma & Immunology.
Harding, S. M., "The human pharmacology of fluticasone propionate," Respiratory Medicine, 1990, vol. 84, Suppl. A, pp. 25-29, Baillière Tindall.
Herrero, Vanrell R., "Preservatives in Ophthalmic Formulations: An Overview," Arch Soc Esp Oftalmol, 2007, vol. 82, pp. 531-532.
Hodges, N. A., et al., "Preservative Efficacy Tests in Formulated Nasal Products: Reproducibility and Factors Affecting Preservative Activity," J. Pharm. Pharmacol., 1996, vol. 48, pp. 1237-1242.
Hodges, Norman, et al., "Antimicrobial Preservative Efficacy Testing," Handbook of Microbiological Quality Control, Pharmaceuticals and Medical Devices, 2000, p. 168 plus cover page and publication pages, Taylor & Francis and Rosamund M. Barid, Norman A. Hodges, and Stephen P. Denyer.
Holgate, Stephen T., Difficult Asthma, 1999, cover page and publishing information, Martin Dunitz Ltd.
Howarth, P. H., "A comparison of the anti-inflammatory properties of intranasal corticosteroids and antihistamines in allergic rhinitis," Allergy 2000, vol. 62, pp. 6-11, Munksgaard 2000.
Howland, III, W. C., "Fluticasone propionate: topical or systemic effects?" Clinical and Experimental Allergy, 1996, vol. 26, Suppl. 3, pp. 18-22, Blackwell Science Ltd.
Isogai, Mitsutaka, et al., "Binding affinities of mometasone furoate and related compounds including its metabolites for the glucocorticoid receptor of rat skin tissue," J. Steroid Biochem. Molec. Biol., 1993, vol. 44, No. 2, pp. 141-145, Peragom Press Ltd.
European Search Report dated May 12, 2009, EP 09075101, 2 pages.
Settipane, Guy, et al., "Triamcinolone acetonide aqueous nasal spray in patients with seasonal ragweed allergic rhinitis: a placebo-controlled, double-blind study," Clinical Therapeutics, 1995, vol. 17, No. 2, pp. 252-263.
Shapiro, Elliot L., et al., "17 heteroaroyl esters of corticosteroids 2. 11β-hydroxy series," Journal of Medicinal Chemistry, vol. 30, No. 9, 1987, pp. 1581-1588, American Chemical Society.
Shapiro, Elliot, et al., "17-esters and 17,21-diesters of 9-α, 11-β-dichlorocorticoids. Synthesis and anti-inflammatory activity," Steroids, vol. 9, No. 2, pp. 143-156, Feb. 1967.
Shapiro, Elliot L., et al., "Synthesis and structure-activity studies of corticosteroid 17-heterocyclic aromatic esters. 1. 9α,11β-dichloro series," Journal of Medicinal Chemistry, vol. 30, No. 6, pp. 1068-1073, 1987, American Chemical Society.
Shenfield, Gillian M., "Fixed drug combinations: which ones can be recommended?" Current Therapeutics, Dec. 1986, pp. 15, 16, 22-24, 27-29.
Simpson, Richard J., "Budesonide and terfenadine, separately and in combination, in the treatment of hay fever," Annals of Allergy, Dec. 1994, vol. 73, pp. 497-502 plus cover page and publication pages, American College of Allergy and Immunology.
Smith, Carolyn L, et al., "In vitro glucocorticoid receptor binding and transcriptional activation by topically active glucocorticoids," Arzneim-Forsch./Drug Res., 1998, vol. 48 (II), No. 9, pp. 956-959.
Smith, N., et al., "Comparison of the electroosmotic flow profiles and selectivity of stationary phases used in capillary electrochromatography," Journal of Chromatography A., vol. 832, 1999, pp. 41-54, Elsevier Science B.V.
Souness, et al., "Immunosuppressive and anti-inflammatory effects of cyclic AMP phosphodiesterase (PDE) type 4 inhibitors," Immunopharmacology, 2000, vol. 47, pp. 127-162, Elsevier Science B.V.
Spector, Sheldon, "Ideal pharmacotherapy for allergic rhinitis," J Allergy Clin Immunol, 1999, vol. 103, No. 3, Part 2, pp. S386-S387, Mosby, Inc.
Stempel, David A., et al., "Treatment of allergic rhinitis: an evidence-based evaluation of nasal corticosteroids versus nonsedating antihistamines," The American Journal of Managed Care, Jan. 1998, vol. 4, No. 1, pp. 89-96.
Study No. 03DMW062—"Pharmacokinetics of GW685698X and CCI18781 (fluticasone propionate) when co-administered by the intratracheal or intravenous route to the anaesthetised white pig," 2004, 21 pages.
Study No. B30947—"The Pharmacokinetics of GW685698X and CCI18781 following intratracheal co-administration to the anaesthetised white pig," 2003, 20 pages.
Szefler, Stanley J., et al., Chapter 21, "Glucocorticoids n severe asthma: mechanisms of action and route of administration," Difficult Asthma, pp. 371-375, Martin Dunitz Ltd, 1999.
Tanaka, Akira, et al., "Synthesis of 4H-furo[3,2-b]indole derivatives. III (1). Preparation of 4H-furo[3,2-b]indole-2-carboxylic acid derivatives," vol. 16, pp. 785-788, Jun. 1979, HeteroCorporation.
The United States Pharmacopoeia, 23rd Edition, U.S. Pharmacopoeia Convention, Inc., 1995, pp. 1843-1844, "Physical Tests / X-ray Diffraction (941)."
Togashi, Teiji, et al., 9-fluoro-11β, 17, 21-trihyrdroxy-16α-methyl-1,4-pregnadiene-3, 20-dione 21-cyclohexanecarboxylate 17-cyclopropanecarboxylate (ST126); Pharmacometrics, 2002, vol. 63, No. 5/6, pp. 61-77.
Ueno, Hiroaki, et al., "Synthesis and evaluation of antiinflammatory activities of a series of corticosteroid 17α-esters containing a functional group," Journal of Medicinal Chemistry, vol. 34, No. 8, 1991, pp. 2468-2473.
Undem, Bradley J., et al., "Neural integration and allergic disease," J Allergy Clin Immunol, 2000, vol. 106, No. 5, pp. S213-S220, Mosby, Inc.
Van As, Andre, et al., "Once daily flluticasone propionate is as effective for perennial allergic rhinitis as twice daily beclomethasone dipropionate," J. Allergy Clin. Immunol., 1993, vol. 91, No. 6, pp. 1146-1154.
Van Bavel, , J. H., et al., "Ocular efficacy and clinician overall evaluation of intranasal fluticasone proprionate (FP) versus loratadine (LOR) in seasonal allergic rhinitis (SAR)," Annals of Allergy, Asthma, & Immunology, 1997, vol. 78, p. 128, Abstract P101.
Van Der Molen, T., et al., "Effects of the long acting β agonist formoterol on asthma control in asthmatic patients using inhaled corticosteroids," Thorax, vol. 52, 1996, pp. 535-539 plus information page.
Vanrell, Herrero, "Preservatives in ophthalmic formulations: an overview," Arch Soc Esp Oftalmol, 2007, vol. 82, pp. 531-532.
Veramyst™ (fluticasone furoate) Nasal Spray, GlaxoSmithKline, 2007, Summary Sheet, pp. 1-20.
Wang, De-Yun, "Treatment of Allergic Rhinitis: H1-Antihistamines and Intranasal Steroids," Current Drug Targets—Inflammation & Allergy, 2002, vol. I, pp. 215-220, Bentham Science Publishers Ltd.
Wenkert, Ernest, et al., "Short syntheses of furan and catechol derivatives. A synthesis of hydrourushiol," Journal American Chemical Society, vol. 105, No. 7, pp. 2021-2029, 1983, American Chemical Society.
Westlund, Ronald, et al., "Fluticasone propionate aqueous nasal spray 200 mg once daily provides relief of ocular symptoms associated with seasonal allergic rhinitis," 57th Annual Meeting of the American Academy of Allergy, Asthma and Immunology, New Orleans, Louisiana, Mar. 16-21, 2001, Abstract No. 522, 1 page.
Wiseman, Lynda R., et al., "Intranasal Fluticasone Propionate: A Reappraisal of its Pharmacology and Clinical Efficacy in the Treatment of Rhinitis," Drugs, 1997, vol. 53, No. 5, pp. 885-907, Adis International Limited.
Woodford, R., et al., "Activity and bioavailability of a new steroid (Timobesone acetate) in cream and ointment compared with Lidex and Dermovate creams and ointments and Betnovate cream," International Journal of Pharmaceutics, 1985, vol. 26, pp. 145-155, Elsevier Science Publishers B.V. (Biomedical Division).

(56) References Cited

OTHER PUBLICATIONS

World Review 2001: The Pharmaceutical Market, vol. 1 International, IMS Health, 2001, cover, preface, and copyright pages plus pp. 4-42 and 5-1 through 5-11, IMS A.G.
Foreign communication from a related counterpart application—Pre-Grant Opposition, 1696/MUMNP/2009, Jun. 27, 2012, 124 pages.
PCT/EP2007/057695, International Search Report and Written Opinion, Oct. 28, 2008, 11 pages.
Johansson, Gunnar, et al., "Comparison of salmeterol/fluticasone propionate combination with budesonide in patients with mild-to-moderate asthma," http://www.medscape.com/viewarticle/406237_print, [Clin Drug Invest, vol. 21, No. 9, 2001, pp. 633-642], Adis International Limited.
Johnson, Malcom, "Development of fluticasone propionate and comparison with other inhaled corticosteroids," J Allergy Clin Immunol, Apr. 1998, vol. 101, No. 4, Part 2, pp. S434-S439, Mosby, Inc.
Juniper, E. F., et al., "Comparison of beclomethasone dipropionate aqueous nasal spray, astemizole, and the combination in the prophylactic treatment of ragweed pollen-induced rhinoconjunctivitis," Journal of Allergy and Clinical Immunology, Mar. 1989, vol. 83, No. 3, cover and publication pages, pp. 627-633, American Academy of Allergy and Immunology, C.V. Mosby Co.
Juniper, Elizabeth F., et al., "Impact of inhaled salmeterol/fluticasone propionate combination product versus budesonide on the health-related quality of life of patients with asthma," Am J Respir Med, vol. 1, No. 6, 2002, pp. 435-440, Adis International Limited.
Kenley, Richard A., et al., "An automated, column-switching HPLC method for analyzing active and excipient materials in both cream and ointment formulations," Drug Development and Industrial Pharmacy, vol. 11, No. 9 & 10, 1985, pp. 1781-1796, Marcel Dekker, Inc.
Kertesz, Denis J., et al., "Thiol esters from steroid 17β-carboxylic acids: carboxylate activation and internal participation by 17 α-acylates," J. Org. Chem., vol. 51, 1986, pp. 2315-2328 (14 pages).
Knobil, K., et al., "Adding salmeterol is more effective than increasing the dose of fluticasone for patients with asthma who are symptomatic on low dose fluticasone," European Respiratory Journal, vol. 12, Suppl. 29, Dec. 1998, pp. 19s-20s.
Kooreman, H. J., et al., "The synthesis of 17-esters of corticosteroids protection of 11β-hydroxyl of the trimethylsilyl group," Synthetic Communications, vol. 1, No. 2, pp. 81-87, 1971, Marcel Dekker, Inc.
Laforce, Craig F., et al., "Fluticasone propionate: an effective alternative treatment for seasonal allergic rhinitis in adults and adolescents," The Journal of Family Practice, 1994, vol. 38, No. 2 (Feb.), pp. 145-152, Appleton & Lange.
Lane, S. J., et al., "Evaluation of a new capillary electrochromatography/mass spectrometry interface using short columns and high field strengths for rapid and efficient analyses," Rapid Communications in Mass Spectrometry, vol. 10, 1996, pp. 733-736, John Wiley & Sons, Ltd.
Lewis, Sarah A., et al., "Association of specific allergen sensitization with socioeconomic factors and allergic disease in a population of Boston women," J Allergy Clin Immunol, vol. 107, No. 4, Apr. 2001, pp. 615-622, Mosby, Inc.
Li, Zheng, et al., "Synthesis of aryl 5-(2-chlorophenyl)-2-furoates under phase transfer catalysis," Synthetic Communications, vol. 32, No. 20, pp. 3081-3086, 2002, Marcel Dekker, Inc.
Linder, A., "Symptom scores as measures of the severity of rhinitis," Clinical Allergy, 1988, vol. 18, pp. 29-37.
Lumry, William R., "A review of the preclinical and clinical data of newer intranasal steroids in the treatment of allergic rhinitis," J Allergy Clin Immunol, Oct. 1999, vol. 104, No. 4, Part 1, pp. S150-S158 plus correction p. 394 dated Feb. 2000, Mosby, Inc.
Lutsky, B. N., et al., "A novel class of potent topical antiinflammatory agents: 17-benzoylated, 7α-halogeno substituted corticosteroids," Arzneim.-Forsch./Drug Res., 1979, vol. 29 (II), No. 11, pp. 1662-1667.
Lyseng-Williamson, Katherine A., et al., "Inhaled salmeterol/fluticasone propionate combination in chronic obstructive pulmonary disease," Am J Respir Med, vol. 1, No. 4, 2002, pp. 273-282, Adis International Limited.
Mahoney, Janette M., et al., "Drug effects on the neovascularization response to silver nitrate cauterization of the rat cornea," Current Eye Research, vol. 4, No. 5, 1985, pp. 531-535, IRL Press Limited, Oxford, England.
Malhotra Exhibit A, Aug. 2011, 7 pages.
Malhotra Exhibit B, Aug. 2011, 6 pages.
Maus Exhibit B, Aug. 2011, 2 pages.
May, Percy, et al., "May's Chemistry of Synthetic Drugs," Fifth Edition, 1964, pp. 12-17 plus cover and publishing pages, Longmans.
McNeely, Wendy, et al., "Intranasal Azelastine: A Review of its Efficacy in the Management of Allergic Rhinitis," Drugs, Jul. 1998, vol. 56, No. 1, pp. 91-114, Adis International Limited.
Mealy, N. E., et al., "Ciclesonide: treatment of allergic rhinitis antiallergy/antiasthmatic," XP009041019, Drugs of the Future, vol. 26, No. 11, Nov. 2001, pp. 1033-1039, Prous Science.
Meltzer, Eli O., "Allergic rhinitis: Managing the pediatric spectrum," Allergy and Asthma Proceedings, Jan.-Feb. 2006, vol. 27, No. 1, pp. 2-8, Oceanside Publications, Inc., U.S.A.
Meltzer, et al., "Onset of therapeutic effect of fluticasone propionate aqueous nasal spray," Annals of Allergy, Asthma, & Immunology, Mar. 2001, vol. 86, No. 3, pp. 286-291.
Millard, Jeffrey W., et al., "Solubilization by cosolvents establishing useful constants for the log-linear model," International Journal of Pharmeceutics, vol. 245, 2002, pp. 153-166, Elsevier Science B.V.
Mistry, Nisha, et al., "Characterisation of impurities in bulk drug batches of fluticasone propionate using directly coupled HPLC-NMR spectroscopy and HPLC-MS," Journal of Pharmaceutical and Biomedical Analysis, vol. 16, 1997, pp. 697-705, Elsevier Science B.V.
Mistry, Nisha, et al., "Impurity profiling in bulk pharmaceutical batches using 19F NMR spectroscopy and distinction between monomeric and dimeric impurities by NMR-based diffusion measurements," Journal of Pharmaceutical and Biomedical Analysis, vol. 19, 1999, pp. 511-517, Elsevier Science B.V.
Möllmann, Helmut, et al., "Pharmacokinetic-Pharmacodynamic Correlations of Corticosteroids," Chapter 14, Handbook of pharmacokinetic/pharmacodynamic correlation, 323-336, 1995, CRC Press.
Moreno-Vargas, et al., "Synthesis and glycosidase inhibitory activities of 5-(1'4'-dideoxy-1'4'-imino-•-erythrosyl)-2-methyl-3-furoic acid (=5-[ (3S,4R)-3,4-dihydroxypyrrolidin-2-yl]-2-methylfuran-3-carboxylic acid) derivatives: new leads as selective α-•-fucosidase and β-galactosidase inhibitors," Helvetica Chimica Acta, vol. 86, pp. 1894-1913, 2003.
Naedele-Risha, Ronnann, et al., "Dual components of optimal asthma therapy: scientific and clinical rationale for the use of long acting β-agonists with inhaled corticosteroids," JAOA, vol. 101, No. 9, Sep. 2001, pp. 526-533.
Nasaonex® (mometasone furoate monohydrate) Nasal Spray, Physicians' Desk Reference®, Product Information, 2002, pp. 3131-3135, Schering, Key Pharmaceuticals, Inc.
Nathan, Robert A., et al., "A once daily fluticasone propionate aqueous nasal spray is an effective treatment for seasonal allergic rhinitis," Annals of Allergy, Sep. 1991, vol. 67, pp. 332-338.
Nelson, Harold, S., et al., Fluticasone propionate-salmeterol combination provides more effective asthma control than low-dose inhaled corticosteroid plus montelukast, J Allergy Clin Immunol, vol. 106, No. 6, Dec. 2000, pp. 1088-1095, Mosby, Inc.
Nielsen, Lars P., et al., "Comparison of Intranasal Corticosteroids and Antihistamines in Allergic Rhinitis: A Review of Randomized, Controlled Trials," Am J Respir Med. 2003, vol. 2, No. 1, cover and publishing pages, pp. 55-65., Adis International Limited.
Nielsen, Lars Peter, et al., "Intranasal corticosteroids for allergic rhinitis: superior relief?" Drugs, 2001, vol. 61, No. 11, pp. 1563-1579 plus cover and publishing pages, Adis International Limited.
Notice of Non-responsive Amendment dated Jul. 6, 2011 (3 pages), U.S. Appl. No. 12/374,523, filed Jan. 21, 2009.
Notice of Opposition to the grant of patent on Patent Application No. 762/2001 (140397) (Pakistan), 2010, 10 pages.
Observations on patentability of the object of the patent application PV 2003-352 (Czech Republic), 2003, 12 pages.
O'Conner, B. J., "Combination therapy," Pulmonary Pharmacology and Therapeutics, vol. 11, 1998, pp. 397-399, Academic Press.

(56) References Cited

OTHER PUBLICATIONS

Office Action (Final) dated May 3, 2011 (8 pages), U.S. Appl. No. 12/374,523, filed Jan. 21, 2009.
Office Action dated Apr. 7, 2011 (3 pages) from counterpart application, AU2009243420.
Office Action dated Aug. 31, 2010 (6 pages), U.S. Appl. No. 12/374,523, filed Jan. 21, 2009.
ABPI Compendium of Data Sheets and Summaries of Product Characteristics, 1999-2000, cover page, p. 43 and index p. 1882, Datapharm Publications Limited, London.
ABPI Data Sheet Compendium, 1995-96, cover page plus pp. 38-39, Datapharm Publications Limited, London.
Aigbirhio, Franklin I., et al., "Automated radiosynthesis of no-carrier-added [S-fluoromethyl-18F]Fluticasone propionate as a radiotracer for lung deposition studies with PET," Journal of Labelled Compounds and Radiopharmaceuticals, vol. 39, No. 7, 1997, pp. 569-584, John Wiley & Sons, Ltd.
Akerlund, Anders, et al., "Clinical trial design, nasal allergen challenge models, and considerations of relevance to pediatrics, nasal polyposis, and different classes of medication," J. Allergy Clin Immunol, Mar. 2005, vol. 115, No. 3, pp. S460-S482.
Applicant response to foreign communication European Patent 1519731, Aug. 11, 2011, 252 pages.
Applicants' response dated Feb. 24, (2010) 2011 (8 pages) in U.S. Appl. No. 12/374,523, filed Jan. 21, 2009.
Applicants' response dated Jun. 22, 2011 (9 pages) U.S. Appl. No. 12/374,523, filed Jan. 21, 2009.
Applicants' response dated Oct. 6, 2010 (8 pages) U.S. Appl. No. 12/374,523, filed Jan. 21, 2009.
Applicants' response dated Sep. 6, 2011 (8 pages) U.S. Appl. No. 12/374,523, filed Jan. 21, 2009.
Applicant response to foreign communication—CA 2489427, Dec. 20, 2010, 10 pages.
Applicant response to foreign communication—EP 03738280.1 (EP Patent 1519731), Sep. 6, 2010, 15 pages.
Applicant response to foreign communication—EP 03738280.1, Jan. 18, 2008, 14 pages.
Applicant response to foreign communication—EP 03738280.1, May 22, 2006, 36 pages.
Applicant response to foreign communication—KR 10-2004-7020819, Dec. 27, 2010, 18 pages.
Astelin® (azelastine hydrochloride) Nasal Spray, Physicians' Desk Reference, 2002, pp. 3339-3340 plus one page Product Information, Wallace Laboratories.
Astelin (azelastine hydrochloride) Nasal Spray, 2006, U.S. Physicians Desk Reference, pp. 1876-1877 plus cover page, MedPointe Pharmaceuticals.
Astepro (azelastine HCI) Nasal Spray 0.15%, Meda Pharmaceuticals Inc., Sep. 2, 2009, Press Release, pp. 1-4.
Aurora, Jack, "Nasal Delivery; Development of Nasal Delivery Systems: A Review," Drug Delivery Technology, vol. 2, No. 7, Oct. 2002, 8 pages, http://www.drugdeliverytech.com/ME2/Segments/Publications/Article&id=9EB19EB2F29F462089CE081473F5F3CA.
Austin, R.J.H., et al., "Mometasone furoate is a less specific glucocorticoid than fluticasone propionate," European Respiratory Journal, 2002, vol. 20, pp. 1386-1392.
Avicel® RC/CL, Microcrystalline Cellulose and Carboxymethylcellulose Sodium, NF Dispersible Cellulose, BP, Specifications and Analytical Methods, RC-16 Updated Oct. 1995 (Feb. 1999), 6 pages, FMC Corporation.
Azelastine, STN Registry No. 58581-89-8, STN Registry File, Retrieved Nov. 23, 2010, p. 1.
Baena-Cagnani, Carlos E., "Safety and Tolerability of Treatments for Allergic Rhinitis in Children," Drug Safety, 2004, vol. 27, No. 12, pp. 883-898, ADIS Data Information BV.
Banov, Charles H., et al., "Once daily intranasal fluticasone propionate is effective for perennial allergic rhinitis," Annals of Allergy, Sep. 1994, vol. 73, pp. 240-246.

Barnes, M. L., et al., "Effects of levocetirizine as add-on therapy to fluticasone in seasonal allergic rhinitis," Clinical and Experimental Allergy, 2006, vol. 36, pp. 676-684, Blackwell Publishing Ltd.
Barnes, Peter J., "Chronic obstructive pulmonary disease: new opportunities for drug development," TiPS, vol. 19, Oct. 1998, pp. 415-423, Elsevier Science Ltd.
Barnes, Peter J., "Efficacy of inhaled corticosteroids in asthma," The Journal of Allergy and Clinical Immunology, vol. 102, No. 4, Part 1, Oct. 1998, pp. 531-538, Mosby, Inc.
Barnes, Peter J., "Novel approaches and targets for treatment of chronic obstructive pulmonary disease," American Journal of Respiratory and Critical Care Medicine, vol. 160, 1999, pp. S72-S79.
Baumgarten, C., et al., "Initial treatment of symptomatic mild to moderate bronchial asthma with the salmeterol/fluticasone propionate (50/250 µg) combination product (SAS 40023)," European Journal of Medical Research, Jan. 29, 2002, vol. 7, pp. 1-7, I. Holzapfel Publishers.
Berge, Stephen M., et al., "Pharmaceutical Salts," Journal of Pharmaceutical Sciences, vol. 66, No. 1, Jan. 1977, pp. 1-19.
Berstein, D. I., et al., "Treatment with intranasal fluticasone propionate significantly improves ocular symptons in patients with seasonal allergic rhinitis," Clinical and Experimental Allergy, 2004, vol. 34, pp. 952-957, Blackwell Publishing Ltd.
Biggadike, Keith, "Fluticasone furoate/fluticasone propionate—different drugs with different properties," Letter to the Editor, The Clinical Respiratory Journal, pp. 183-184, 2011, Blackwell Publishing Ltd.
Block, John H., et al., "Inorganic Medicinal and Pharmaceutical Chemistry," 1986, cover, publication, and preface pages plus p. 100, Indian Edition, Varghese Publishing House, Bombay, India.
Bowler, Simon, "Long acting beta agonists," Australian Family Physician, vol. 27, No. 12, Dec. 1998, pp. 1115, 1117-1118.
Brooks, Carter D., et al., "Spectrum of seasonal allergic rhinitis symptom relief with topical corticoid and oral antihistamine given singly or in combination," American Journal of Rhinology, May-Jun. 1996, vol. 10, No. 3, pp. 193-199.
Bryson, Harriet M., et al., "Intranasal fluticasone propionate: a review of its pharmacodynamic and pharmacokinetic properties, and therapeutic potential in allergic rhinitis," Drugs, 1992, vol. 43, No. 5, pp. 760-775, Adis International Limited.
Busse, William, et al., "Steroid-sparing effects of fluticasone propionate 100 µg and salmeterol 50 µg administered twice daily in a single product in patients previously controlled with fluticasone propionate 250 µg. administered twice daily," J Allergy Clin Immunol, vol. 111, No. 1, Jan. 2003, pp. 57-65, Mosby, Inc.
Busse, William W., et al., "Corticosteroid-sparing effect of azelastine in the management of bronchial asthma," XP-000604179, American Journal of Respiratory and Critical Care Medicine, 1996, pp. 122-127, vol. 153.
CAS Registry No. 102113-40-6, 2004, 1 page, ACS on STN.
CAS Registry No. 90566-53-3, "Fluticasone," Entered STN: Nov. 16, 1984, 1 page, © 2008 ACS on STN.
Chapman, Richard W., et al., "Anti-inflammatory activity of inhaled mometasone furoate in allergic mice," Arzneim.-Forsch./Drug Res., 1998, vol. 48, No. 4, pp. 384-391.
Cipla Annual Report Extract, 2010 (report shows that they launched an FF+azelastine product in 2010), 103 pages.
Cipla Sixty-Ninth Annual Report 2004-2005, cover pages, information page, plus pp. 3, 5, and 44.
Cipla's response to Statement of Opposition for EP1519731, 11 pages.
Comparative data of azelastine with steroids, 2011, 4 pages.
Daley-Yates, Peter T., et al., "Systemic bioavailability of fluticasone propionate administered as nasal drops and aqueous nasal spray formulations," Br J Clin Pharmacol., 2001, vol. 51, pp. 103-105, Blackwell Science Ltd.
Declaration of Geena Malhotra for EP1519731 dated Aug. 11, 2011, 4 pages.
Declaration of Joachim Maus for EP1519731 dated Aug. 10, 2011, 6 pages.
Derby, Laura, et al., "Risk of cataract among users of intranasal corticosteroids," J Allergy Clin Immunol, 2000, vol. 105, No. 5, pp. 912-916, Mosby, Inc.

(56) References Cited

OTHER PUBLICATIONS

Dewester, Jeffrey, et al., "The efficacy of intranasal fluticasone propionate in the relief of ocular symptoms associated with seasonal allergic rhinitis," Allergy and Asthma Proc., Sep.-Oct. 2003, vol. 24, No. 5, pp. 331-337.
Dictionary of Organic Compounds, definition of "fluticasone," Sixth Edition, 1996, vol. 1, p. 3234 plus cover and publishing pages, Chapman & Hall.
Office Action dated Jul. 11, 2011—20632 IL, 3 pages.
Office Action dated Mar. 29, 2011 (3 pages) from counterpart application, AU2009243422.
Office Action dated Nov. 30, 2010 (16 pages), U.S. Appl. No. 12/374,523, filed Jan. 21, 2009.
European Search Report dated May 12, 2009, EP 09075100, 3 pages.
Sandham, David A., et al., "Synthesis and biological properties of novel glucocorticoid androstene C-17 furoate esters," Bioorganic & Medicinal Chemistry, 2004, vol. 12, pp. 5213-5224, Elsevier Ltd.
Scadding, Glenis K., et al., "Clinical and physiological effects of fluticasone propionate aqueous nasal spray in the treatment of perennial rhinitis," Rhinology, 1991, Suppl. 11, pp. 37-43.
Schmidt, Bernhard M. W., et al., "The New Topical Steroid Ciclesonide is Effective in the Treatment of Allergic Rhinitis," Journal of Clinical Pharmacology, 1999, vol. 39, pp. 1062-1069, American College of Clinical Pharmacology.
Ong, John T. H., et al., "Intrinsic potencies of novel thiol ester corticosteroids RS-85095 and RS-21314 as compared with clobetasol 17-propionate and fluocinonide," Arch Dermatol, vol. 125, Dec. 1989, pp. 1662-1665.
Ong, John T. H., et al., "Micellar solubilization of timobesone acetate in aqueous and aqueous propylene glycol solutions of nonionic surfactants," Pharmaceutical Research, vol. 5, No. 11, 1988, pp. 704-708, Plenum Publishing Corporation.
Onrust, Susan B., et al., "Mometasone furoate: a review of its intranasal use in allergic rhinitis," Drugs, vol. 56, No. 4, Oct. 1998, pp. 725-745, Adis International Limited.
Opponent's R116 Submission for European Patent No. 1519731, 18 pages, 2012.
Opponent's Statement of Opposition for European Patent No. 1519731, 15 pages, 2011.
Opponent's submission dated Oct. 6, 2011 to European Patent No. 1519731, 2 pages.
Opponent's submission dated Sep. 23, 2011 regarding additional documents on European Patent No. 1519731, 2 pages.
Opponent's submission dated Sep. 23, 2011 regarding list of attendees at oral proceedings on European Patent No. 1519731, 1 page.
Patentee's response of Sep. 6, 2010 of European Patent No. 1519731, 49 pages.
Opposition to EP 1518731, Aug. 8, 2011, 19 pages.
Patentee's submission dated Sep. 19, 2011 on European Patent No. 1519731, 1 page.
Patentee's submission dated Sep. 29, 2011 regarding list of attendees at oral proceedings on EP Patent No. 1519731, 1 page.
Pettersson, Bertil, et al., "Re-evaluation of the classical mycoplasma lipophilum cluster (Weisburg, et al., 1989) and description of two new clusters in the hominis group based on 16S rDNA sequences," International Journal of Systematic and Evolutionary Microbiology, 2001, vol. 51, pp. 633-643, IUMS.
Phillips, G. H., et al., "Synthesis and structure—activity relationships in a series of anti-inflammatory corticosteroid analogues, halomethyl androstane—17β-carbothioates and—17β-carboselenoates," Journal of Medicinal Chemistry, 1994, vol. 37, No. 22, pp. 3717-3729, American Chemical Society.
Popper, Thomas L., et al., "Structure-activity relationships of a series of novel topical corticosteroids," J. steroid Biochem., 1987, vol. 27, No. 4-6, pp. 837-843 Pergamon Journals Ltd.
Portmann, D. et al., Acceptability of local treatment of allergic rhinitis with a combination of a corticoid (beclomethasone) and an antihistaminic (azelastine), XP-002252974, 2000, 1 page, Medline.
Pre-Grant Opposition, Indian Patent Application 2092/KOLNP/2007 dated Jun. 8, 2007, 183 pages.
Prescribing Information for Asterpro®, Nov. 2010, 20 pages, Meda Pharmaceuticals Inc.
Prescribing Information for Rhinocort Aqua®, Dec. 2010, 32 pages, AstraZeneca LP.
Preservative, definition of. Composite definition of preservative in the Medical dictionary, from internet site http:// medical-dictionary.thefreedictionary.com/preservative, Nov. 4, 2009, 3 pages.
Prescribing Information Flonase® (fluticasone proprionate) Nasal Spray 50 mcg, Mar. 2004, pp. 1-13, GlaxoSmithKline.
Product Information Rhinocort Aqua® (budesonide) Nasal Spray 32 mcg, Jan. 2005, 2 pages.
Product Information, Nasonex® (mometasone furoate monohydrate) Nasal Spray 50 mcg, Aug. 2001, 22 pages, Schering Corporation.
Product Specification Bulletin, Avicel® CL-611, Bulletin AVC611-SPEC-02/09.RS, Feb. 2009, 2 pages, FMC Corporation.
Product Specification Bulletin, Avicel® RC-591, Bulletin AVC591-SPEC-02/09.RS, Feb. 2009, 2 pages, FMC Corporation.
Rapid Response Report: Summary with Critical Appraisal, "Fluticasone Furoate versus Fluticasone Propionate for Seasonal Allergic Rhinitis: A Review of the Clinical and Cost Effectiveness," Jun. 13, 2011, 8 pages, Canadian Agency for Drugs and Technologies in Health.
Ratner, Paul H., et al., "A Comparison of the Efficacy of Fluticasone Propionate Aqueous Nasal Spray and Loratadine, Alone and in Combination, for the Treatment of Seasonal Allergic Rhinitis," The Journal of Family Practice, Aug. 1998, vol. 47, No. 2, pp. 118-125 plus cover and publishing pages, Appleton & Lange.
Ratner, Paul H., et al., "Combination therapy with azelastine hydrochloride nasal spray and fluticasone propionate nasal spray in the treatment of patients with seasonal allergic rhinitis," Annals of Allergy, Asthma & Immunology, Jan. 2008, vol. 100, pp. 74-81 plus cover and publishing pages.
Reddy, Indra K., "Ocular Therapeutics and Drug Delivery: A Multi-Disciplinary Approach," 1996, pp. 382-385 plus cover and publishing pages, Technomic Publishing Company, Inc.
Result of oral proceedings dated Oct. 12, 2011 of EP Patent No. 1519731, 5 pages.
Safety Data Sheet No. 110536, Jun. 23, 2008, Version 13, Beconase Hayfever Allergy Spray, 5 pages, GlaxoSmithKline.
Safety Data Sheet No. 110556, Jul. 4, 2008, Version 14, Flonase Nasal Spray, 5 pages, GlaxoSmithKline.
Sakagami, Masahiro, et al., "Mucoadhesive BDP microspheres for powder inhalation-their unique pharmacokinetic-pharmacodynamic profiles," Respiratory Drug Delivery, vol. VI, pp. 193-199, 1998.
Salib, Rami Jean, et al., "Safety and Tolerability Profiles of Intranasal Antihistamines and Intranasal Corticosteroids in the Treatment of Allergic Rhinitis," Drug Safety, 2003, vol. 26, No. 12, pp. 863-893 plus cover and publishing page, ADIS Data Information BV.
Clincaltrials.gov, "Efficacy and safety of mometasone furoate plus azelastine HCl combination versus mometasone furoate alone or azelastine alone in patients with perennial allergic rhinitis (NCT01470053)," http://clinicaltrials.gov/ct2/show/NCT01470053, Nov. 8, 2011, 3 pages.
1 page summary of "Evaluation of fluticasone propionate aqueous nasal spray taken alone and in combination with cetirizine in the prophylactic treatment of seasonal rhinitis," Drug Investigation, Oct. 1994, vol. 8, Issue 4, pp. 225-233.
Finn, Jr., A. F., et al., 1 page abstract of "Efficacy of three different dosing regimens of fluticasone propionate (FP) aqueous nasal spray in the treatment of perennial nonallergic rhinitis (PNAR)," J Allergy Clin Immunol, Jan. 1997, Ref. No. 1787.
Graft, David, et al., "A placebo- and active-controlled randomized trial of prophylactic treatment of seasonal allergic rhinitis with mometasone furoate aqueous nasal spray," J Allergy Clin Immunol, Oct. 1996, vol. 98, No. 4, pp. 724-731.
Marazzi, P., et al., 1 page abstract of "Prophylactic use of once-dailly mometasone furoate (Nasonex) aqueous nasal spray in patients with seasonal allergic rhinitis," J Allergy Clin Immunol, Jan. 1997, Ref. No. 1789.
Nakabayashi, S., et al., 1 page abstract of "The effect of initial treatment by FP aqueous nasal spray in patients with Japanese cedar pollinosis," Sep. 1996, vol. 99, No. 9, pp. 1162-1171.

(56) References Cited

OTHER PUBLICATIONS

Simon, Michael W., 1 page abstract of "The efficacy of azelastine in the prophylaxis of acute upper respiratory tract infections," Allergy & Immunology, Dec. 2003, vol. 16, No. 4, pp. 275-282.
Small, C. B., et al, 1 page abstract of "Prophylaxis of nasal polyprosis after response to treatment with mometasone furoate nasal spray," J Allergy Clin Immunol, vol. 127, No. 2, Ref. No. 466, 2011.
Trangsrud, Amanda J., et al., "Intranasal corticosteroids for allergic rhinitis," Pharmacotherapy, 2002, vol. 22, No. 11, 14 pages.
Yamagishi, Masuo, et al., 1 page abstract of "Azelastine in the treatment and prevention of seasonal grass pollinosis," Practica Oto-Rhino-Laryngologica, 1991, vol. 84, No. 9, pp. 1345-1353.
Applicants' response dated Feb. 24, (2010) 2011 (8 pages) U.S. Appl. No. 12/374,523, filed Jan. 21, 2009.
Baldwin C. M., et al., abstract, "Mometasone furoate: a review of its intranasal use in allegic rhinitis," 2008, 1 page, [Drugs, pp. 1723-1739, vol. 68, No. 12].
Bielory, L., et al., "Impact of mometasone furoate nasal spray on individual ocular symptoms of allergic rhinitis: a meta-analysis," Allergy, 2011, pp. 686-693, vol. 66, John Wiley & Sons A/S.
Clincaltrials.gov, "A study of the effectiveness and safety of mometasone furoate nasal spray (MFNS,SCH032088) for the treatment of nasal polyps (P05604)," http://clinicaltrials.gov/ct2/show/NCT01386125, Mar. 14, 2013, 3 pages, Merck.
Clincaltrials.gov, "Mometasone furoate nasal spray for treatment of nasal polyposis after surgery (study P03218)," http://clinicaltrials.gov/ct2/show/NCT00731185, Aug. 7, 2008, 3 pages, Schering-Plough.
Document submitted in the Opposition proceedings regarding European Patent No. 1519731, D35, Units and Sales for Corticosteroids in 2009 and 2010, Oct. 5, 2011, 3 pages.
Document submitted in the Opposition proceedings regarding European Patent No. 1519731, D36, Stability tests, Oct. 5, 2011, 4 pages.
Foreign communication from a related counterpart application—Pre-Grant Opposition, Indian Application No. 1696/MUMNP/2009, Jun. 27, 2012, 124 pages.
Makihara, Seiichiro, et al., "Early interventional treatment with intranasal mometasone furoate in Japanese cedar/cypress pollinosis: a randomized placebo-controlled trial," Allergology International, 2012, pp. 295-304, vol. 61, No. 2, Japanese Society of Allergology.
"Nasal Polyp," Wikipedia entry, http://en.wikipedia.org/wiki/Nasal_polyp, downloaded from Internet on Apr. 3, 2013, 4 pages.
Office Action dated Apr. 15, 2013 (94 pages), U.S. Appl. No. 13/644,127, filed Oct. 3, 2012.
Office communication dated Jul. 6, 2011 (3 pages), U.S. Appl. No. 12/374,523, filed Jan. 21, 2009.
Office Action dated Jul. 15, 2013 (48 pages), U.S. Appl. No. 13/204,978, filed Aug. 8, 2011.
PCT/EP2007/057695, International Search Report and Written Opinion, Oct. 28, 2008, 16 pages.
PCT/EP2007/057695, International Preliminary Report on Patentability, Feb. 3, 2009, 8 pages.
PCT/GB01/03495, International Preliminary Examination Report, Aug. 30, 2002, 11 pages.
PCT/GB01/03495, International Search Report, Oct. 17, 2001, 2 pages.
Small, Catherine Butkus, et al, "Efficacy and safety of mometasone furoate nasal spray in nasal polyposis," J Allergy Clin Immunol, Dec. 2005, pp. 1275-1281, American Academy of Allergy, Asthma and Immunology.
Stjärne, Pär, et al, "A randomized controlled trial of mometasone furoate nasal spray for the treatment of nasal polyposis," Arch Otolaryngol Head Neck Surg, Feb. 2006, pp. 179-185, vol. 132, American Medical Association.
Stjärne, Pär, et al.,"Use of mometasone furoate to prevent polyp relapse after endoscopic sinus surgery," Mar. 2009, pp. 296-302, Arch Otolaryngol Head Neck Surg, vol. 135, No. 3, American Medical Association.
Vuralkan, Erkan, et al., "Comparison of montelukast and mometasone furoate in the prevention of recurrent nasal polyps," 2012, pp. 5-10, vol. 6, No. 1, Therapeutic Advances in Respiratory Disease.
"Allergic Rhinitis and its Impact on Asthman (ARIA) 2008," European Journal of Allergy and Clinical Immunology, Apr. 2008, 160 pages, vol. 63, No. 86, Wiley-Blackwell, Copenhagen, DK.
"Aria Workshop Report: Allergic Rhinitis and its Impact on Asthma," The Journal of Allergy and Clinical Immunology, Nov. 2001, 205 pages, vol. 108, No. 5, Mosby.
Astelin Product Information, Meda Pharmaceuticals Inc., 8 pages, 2011.
Berger, William E., et al., "Double-blind trials of azelastine nasal spray monotherapy versus combination therapy with loratadine tablets and beclomethasone nasal spray in patients with seasonal allergic rhinitis," Annals of Allergy, Asthma & Immunology, Jun. 1999, pp. 535-541, vol. 82.
Communication of Notice of Opposition in a foreign counterpart application, EP Patent No. 2072051, Nov. 6, 2014, 19 pages.
Comparative Composition data of Azelastine with steriods table filed by patentee, 20632A-EP, Nov. 2, 2010.
Comparative Data Table, Fluticasone Furoate, 4 pages, 2014.
European Sales Data Table, 2001-2005, 3 pages.
Nasacort Product Leaflet, 2010, 5 pages, sanofi-aventis U.S. LLC, Bridgewater, NJ, US.
Opponent/Appellant's Statement of Grounds of Appeal Against the Interlocutory Decision in Oppositon Proceedings in a foreign counterpart application, EP Patent No. EP 1 519 731 B1, May 28, 2012, 62 pages.
Pawankar, Ruby, "Allergic Rhinitis and Its Impact on Asthma: An Evidence-Based Treatment Strategy for Allergic Rhinitis," Asian Pacific Journal of Allergy and Immunology, Mar. 2002, pp. 43-52, vol. 20, No. 1, Allergy, Asthma and Immunology Society of Thailand.
Reichmuth, Daniel, et al., "Present and Potential Therapy for Allergic Rhinitis, A Review," BioDrugs, Dec. 2000, pp. 371-387, vol. 14, No. 6, Adis International Limited.
Reply of Patentee to Grounds of Appeal in a foreign counterpart application, EP Patent No. EP 1 519 731 B1, Feb. 14, 2013, 44 pages.
"Rote Liste," Catalogue of drugs marketed in Germany in the year 2002, entries 07 079 and 07 080 (Allergodil, nasal spray (solution)), and 72 025 (Nasonex, nasal spray (suspension)), 3 pages.
Scadding, G.K., "Clinical assessment of antihistamines in rhinitis," Clinical and Experimental Allergy, 1999, pp. 77-81, vol. 29, No. 3, Blackwell Science Ltd.
Stricker, W.E., et al., Abstract of: "Fluticasone Propionate Aqueous Nasal Spray (FP) and Loratadine (LOR), Alone and in Combination, in the Treatment of Fall Seasonal Allergic Rhinitis (SAR)," Abstracts: Porter Sessions, Jan. 1998, p. 115, vol. 80.
Sur, Denise K., et al., "Treatment of Allergic Rhinitis," American Family Physician, Jun. 15, 2010, pp. 1440-1446, vol. 81, No. 12, American Academy of Family Physicians.
USP Monographs: Flunisolide Nasal Solution, 2013, 2 pages, USPC Official.
Lieberman, Phil, "Treatment Update: Nonallergic Rhinitis," Allergy and Asthma Proceedings, Jul.-Aug. 2001, Abstract, 1 page, vol. 22, No. 4, OcenSide Publications, Inc.
Van Cauwenberge, P., et al., "Consensus Statement on the treatment of allergic rhinitis," Allergy, 2000, pp. 116-134, vol. 55, Munksgaard, UK.
Lieberman, Phil, "Treatment Update: Nonallergic Rhinitis," Allergy and Asthma Proceedings, Jul.-Aug. 2001, pp. 199-202, vol. 22, No. 4, OceanSide Publications, Inc.

COMBINATION OF AZELASTINE AND CICLESONIDE FOR NASAL ADMINISTRATION

CROSS-REFERENCE TO RELATED APPLICATIONS

This application is a Continuation application of and claims priority to U.S. patent application Ser. No. 12/508,393 filed on Jul. 23, 2009, published as U.S. Publication No. 2009/0318397 A1 and entitled "Combination of Azelastine and Steroids," which is a Divisional application of U.S. patent application Ser. No. 10/518,016, filed Jul. 6, 2005, now U.S. Pat. No. 8,168,620, and entitled "Combination of Azelastine and Steroids," which was a filing under 35 U.S.C. 371 of International Application No. PCT/GB03/02557 filed Jun. 13, 2003, entitled "Combination of Azelastine and Steroids," claiming priority of Great Britain Patent Application No. 0213739.6 filed Jun. 14, 2002, which applications are incorporated by reference herein in their entirety.

BACKGROUND OF THE INVENTION

The present invention relates to pharmaceutical products and formulations. More particularly the present invention relates to pharmaceutical products and formulations useful for preventing or minimising allergic reactions. More particularly, but not exclusively, the present invention relates to pharmaceutical products and formulations for nasal and ocular use.

Such allergic reactions commonly comprise the allergy-related and vasomotor-related symptoms and the rhinovirus-related symptoms.

It is known to use antihistamines in nasal sprays and eye drops to treat allergy-related conditions. Thus, for example, it is known to use the antihistamine azelastine (usually as the hydrochloride salt) as a nasal spray against seasonal or perennial allergic rhinitis, or as eye drops against seasonal and perennial allergic conjunctivitis.

It is also known to treat these conditions using a corticosteroid, which will suppress nasal and ocular inflammatory conditions. Among the corticosteroids known for nasal use are, for example, beclomethasone, mometasone, fluticasone, budesonide and ciclesonide. Corticosteroids known for ocular anti-inflammatory use include betamethasone sodium, dexamethasone sodium and prednisolone acetate, for example.

It would be highly desirable, however, to provide a treatment that combines the effects of anti-histamine treatments and steroid treatments, in a pharmaceutically acceptable formulation, which is tolerated in situ, without significantly disrupting the potency of the constituent pharmaceuticals.

We have now found that, very surprisingly, azelastine (4-[(4-Chlorophenyl)methyl]-2-(hexahydro-1-methyl-1H-azepin-4-yl)-1(2H)-phthalazinone), or a pharmaceutically acceptable salt, solvate or physiologically functional derivative thereof, preferably in salt form and even more preferably in the form of the hydrochloride salt, can advantageously be combined with a steroid, or a pharmaceutically acceptable salt, solvate or physiologically functional derivative thereof, to provide a stable, very effective combination product or formulation preferably for nasal or ocular treatment. The combination can provide, in a single administration or dosing regime, the antihistaminic properties of azelastine and the anti-inflammatory (and/or other) properties of the steroid, without any significant interference between the two, or adverse reaction in situ.

SUMMARY OF THE INVENTION

In one aspect the invention provides a pharmaceutical formulation comprising azelastine or a pharmaceutically acceptable salt, solvate or physiologically functional derivative thereof, and a steroid, preferably a corticosteroid, or a pharmaceutically acceptable salt, solvate or physiologically functional derivative thereof, the formulation preferably being in a form suitable for administration nasally or ocularly. In an embodiment, the formulation contains the steroid in an amount from about 50 micrograms/ml to about 5 mg/ml of the formulation. In an embodiment, the formulation contains a suspension containing 0.0005% to 2% (weight/weight of the formulation) of azelastine or a pharmaceutically acceptable salt of azelastine, and from 0.5% to 1.5% (weight/weight of the formulation) of said steroid. In an embodiment, the formulation contains a suspension containing from 0.001% to 1% (weight/weight of the formulation) azelastine, or salt thereof, and from 0.5% to 1.5% (weight/weight of the formulation) steroid.

The term "physiologically functional derivative" as used herein denotes a chemical derivative of any of the specific therapeutic agents described herein having the same or similar physiological function as the free base therapeutic agent and, for example, being convertible in the body thereto. According to the present invention, examples of physiologically functional derivatives include esters.

DETAILED DESCRIPTION OF THE INVENTION

The preferred forms of formulations of the invention are nasal drops, eye drops, nasal sprays, nasal inhalation solutions or aerosols or insufflation powders.

Preferred embodiments of the invention can comprise stable aqueous solutions of azelastine or one or more of its salts, in combination with steroids which may be beclomethasone, mometasone, fluticasone, budesonide or ciclesonide, which can be used in the form of inhalation solution, pressurized aerosol, eye drops or nasal drops, and in a particular preferred embodiment, in the form of a spray (preferably a nasal spray). The spray can, for example, be formed by the use of a conventional spray-squeeze bottle or a pump vaporizer. In addition, it is also possible to use compressed gas aerosols. In a preferred embodiment, 0.03 to 3 mg of azelastine base and 0.05 to 0.15 mg of the steroid should be released per individual actuation.

The formulations preferably contain a preservative and/or stabilizer. These include, for example: ethylene diamine tetraacetic acid (edetic acid) and its alkali salts (for example dialkali salts such as disodium salt, calcium salt, calcium-sodium salt), lower alkyl p-hydroxybenzoates, chlorhexidine (for example in the form of the acetate or gluconate) and phenyl mercury borate. Other suitable preservatives are: pharmaceutically useful quaternary ammonium compounds, for example cetylpyridinium chloride, tetradecyltrimethyl ammonium bromide, generally known as "cetrimide", benzyldimethyl-[2-[2-[p-(1,1,3,3-tetramethyl-butyl)phenoxy]ethoxy]-ammonium chloride, generally known as "benzethonium chloride" and myristyl picolinium chloride. Each of these compounds may be used in a concentration of 0.002 to 0.05%, for example 0.02% (weight/volume in liquid formulations, otherwise weight/weight). Preferred preservatives among the quaternary ammonium compounds are, however, alkylbenzyl dimethyl ammonium chloride and mixtures thereof, for example the compounds generally known as "benzalkonium chloride."

The total amount of preservatives in the formulations (solutions, ointments, etc.) is preferably from 0.001 to 0.10 g, preferably 0.01 g per 100 ml of solution/suspension or 100 g of formulation.

In the case of preservatives, the following amounts of individual substances can, for example, be used: thimero sal 0.002-0.02%; benzalkonium chloride 0.002 to 0.02% (in combination with thimero sal the amount of thimero sal is, for example =0.002 to 0.005%); chlorhexidine acetate or gluconate 0.01 to 0.02%; phenyl mercuric/nitrate, borate, acetate 0.002-0.004%; p-hydroxybenzoic acid ester (for example, a mixture of the methyl ester and propyl ester in the ratio 7:3): preferably 0.05-0.15, more preferably 0.1%.

The preservative used is preferably a combination of edetic acid (for example, as the disodium salt) and benzalkonium chloride. In this combination, the edetic acid is preferably used in a concentration of 0.05 to 0.1%, benzalkonium chloride preferably being used in a concentration of 0.005 to 0.05%, more preferably 0.01%.

In the case of solutions/suspensions reference is always made to percent by weight/volume, in the case of solid or semi-solid formulations to percent by weight/weight of the formulation.

Further auxiliary substances which may, for example, be used for the formulations of the invention are: polyvinyl pyrrolidone, sorbitan fatty acid esters such as sorbitan trioleate, polyethoxylated sorbitan fatty acid esters (for example polyethoxylated sorbitan trioleate), sorbimacrogol oleate, synthetic amphotensides (tritons), ethylene oxide ethers of octylphenolformaldehyde condensation products, phosphatides such as lecithin, polyethoxylated fats, polyethoxylated oleotriglycerides and polyethoxylated fatty alcohols. In this context, polyethoxylated means that the relevant substances contain polyoxyethylene chains, the degree of polymerisation of which is generally between 2 to 40, in particular between 10 to 20. These substances are preferably used to improve the solubility of the azelastine component.

It is optionally possible to use additional isotonization agents. Isotonization agents which may, for example, be used are: saccharose, glucose, glycerine, sorbitol, 1,2-propylene glycol and NaCl.

The isotonization agents adjust the osmotic pressure of the formulations to the same osmotic pressure as nasal secretion. For this purpose, these substances are in each case to be used in such amount that, for example, in the case of a solution, a reduction in the freezing point of 0.50 to 0.56 degree C. is attained in comparison to pure water.

In Example 1, it is possible to use instead of NaCl per 100 ml of solution, for example: Glucose $1H_2O$ 3.81 g; saccharose 6.35 g; glycerine 2.2 g; 1,2-propylene glycol 1.617 g; sorbitol 3.84 g (in the case of mixtures of these substances correspondingly less may optionally be used).

Moreover, it is possible to add thickening agents to solutions according to the present invention to prevent the solution from flowing out of the nose too quickly and to give the solution a viscosity of about 1.5 to 3, preferably 2 mPa.

Such thickening agents may, for example, be: cellulose derivatives (for example cellulose ether) in which the cellulose-hydroxy groups are partially etherified with lower unsaturated aliphatic alcohols and/or lower unsaturated aliphatic oxyalcohols (for example methyl cellulose, carboxymethyl cellulose, hydroxypropylmethylcellulose), gelatin, polyvinylpyrrolidone, tragacanth, ethoxose (water soluble binding and thickening agents on the basis of ethyl cellulose), alginic acid, polyvinyl alcohol, polyacrylic acid, pectin and equivalent agents. Should these substances contain acid groups, the corresponding physiologically acceptable salts may also be used.

In the event of the use of hydroxypropyl cellulose, 0.1% by weight of the formulation, for example, is used for this purpose.

In the event of the use of Avicel RC 591 or CL 611, microcrystalline cellulose and carboxymethyl cellulose sodium commercially available from FMC BioPolymer, 0.65-3.0% by weight of the formulation, for example, is used for the purpose.

It is also possible to add to the formulations buffer substances such as citric acid/sodium hydrogensulphate borate buffer, phosphates (sodium hydrogenorthophosphate, disodium hydrogenphosphate), trometamol or equivalent conventional buffers in order, for example, to adjust the formulations to a pH value of 3 to 7, preferably 4.5 to 6.5.

The amount of citric acid is, for example, 0.01 to 0.14 g, preferably 0.04 to 0.05 g, the amount of disodium hydrogenphosphate 0.1 to 0.5 g, preferably 0.2 to 0.3 g per 100 ml of solution. The weights given relate in each case to the anhydrous substances.

In the case of solutions and suspensions, the maximum total concentration of active agent and buffer is preferably less than 5%, in particular less than 2% (weight/volume).

For the nasal application, a solution or suspension can preferably be used which is applied as an aerosol, i.e. in the form of a fine dispersion in air or in another conventional carrier gas, for example by means of a conventional pump vaporizer.

Application as a dosage aerosol is, however, also possible. Dosage aerosols are defined as being pressure packings which contain the azelastine or its salts in combination with steroid, in the form of a solution or suspension in a so-called propellant. The propellant may be a pressurized liquid chlorinated, fluorinated hydrocarbon or mixtures of various chlorinated, fluorinated hydrocarbons as well as propane, butane, isobutene or mixtures of these among themselves or with chlorinated, fluorinated hydrocarbons which are gaseous at atmospheric pressure and room temperature. Hydrofluorocarbons (HFCs), such as HFC 134a, and HFC 227a can also be used, and are preferred for environmental reasons. The pressure packing has a dosage or metering valve which, on actuation, releases a defined amount of the solution or suspension of the medicament. The subsequent very sudden vaporization of the propellant tears the solution or suspension of azelastine into the finest droplets or minute particles which can be sprayed in the nose or which are available for inspiration into the nose. Certain plastic applicators may be used to actuate the valve and to convey the sprayed suspension into the nose.

In the case of application as an aerosol, it is also possible to use a conventional adapter.

Particularly preferred embodiments of the present invention are hereinafter described and it will of course be appreciated that any of the previous description of suitable ingredients and formulation characteristics can also be applicable to the following products and formulations as provided by the present invention.

It will be appreciated, therefore, that the present invention further provides a pharmaceutical product comprising (i) azelastine, or a pharmaceutically acceptable salt, solvate or physiologically functional derivative thereof, provided in an aerosol formulation preferably together with a propellant typically suitable for MDI delivery, and (ii) at least one steroid, or a pharmaceutically acceptable salt, solvate or physiologically functional derivative thereof, provided in an aerosol formulation preferably together with a propellant typically suitable for MDI delivery, as a combined preparation for simultaneous, separate or sequential use in the treatment of conditions for which administration of one or more anti-histamine and/or one or more steroid is indicated.

The present invention also provides an aerosol formulation preferably suitable for MDI delivery comprising (i) azelastine, or a pharmaceutically acceptable salt, solvate or physiologically functional derivative thereof, and (ii) at least one steroid, or a pharmaceutically acceptable salt, solvate or physiologically functional derivative thereof, together with a propellant.

It will also be appreciated from the above, that the respective therapeutic agents of the combined preparation can be administered simultaneously, either in the same or different pharmaceutical formulations, or separately or sequentially. If there is separate or sequential administration, it will also be appreciated that the subsequently administered therapeutic agents should be administered to a patient within a time scale so as to achieve, or more particularly optimise, the above referred to advantageous synergistic therapeutic effect of a combined preparation as present in a pharmaceutical product according to the present invention.

Suitable propellants for use in pharmaceutical products of formulations as provided by the present invention include 1,1,1,2-tetrafluoroethane (HFA 134a) or 1,1,1,2,3,3,3,-heptafluoropropane (HFA 227), or a combination of both, or mono-fluoro trichloromethane and dichloro difluoromethane, in particular 1,1,1,2-tetrafluoroethane (HFA 134a) or 1,1,1,2,3,3,3-heptafluoropropane (HFA 227), with HFA 134a being preferred.

A pharmaceutical aerosol formulation according to the present invention preferably further comprises a polar cosolvent such as $C_{2-6}$ aliphatic alcohols and polyols, for example ethanol, isopropanol and propylene glycol, with ethanol often being preferred. Preferably, the concentration of the cosolvent is in the range of about 2 to 10% by weight, typically up to about 5%, of the total formulation.

A pharmaceutical aerosol formulation according to the present invention may further comprise one or more surfactants. Such surfactants can be included to stabilise the formulations and for lubrication of a valve system. Some of the most commonly used surfactants in aerosol formulations are oils derived from natural sources, such as corn oil, olive oil, cottonseed oil and sunflower seed oil, and also phospholipids. Suitable surfactants can include lecithin, oleic acid or sorbitan oleate. In an embodiment, the formulation contains from about 50 micrograms to about 1 milligram of surfactant per ml of the formulation.

A further preferred embodiment of the present invention can be where a formulation or product is provided in the form of insufflatable powder, where preferably the maximum particle size of the substance suitably does not exceed 10 μm. Azelastine or its salts and the steroid may be mixed with inert carrier substances or drawn up onto inert carrier substances. Carrier substances which may, for example, be used are: sugars such as glucose, saccharose, lactose and fructose. Also starches or starch derivatives, oligosaccharides such as dextrins, cyclodextrins and their derivatives, polyvinylpyrrolidone, alginic acid, tylose, silicic acid, cellulose, cellulose derivatives (for example cellulose ether), sugar alcohols such as mannitol or sorbitol, calcium carbonate, calcium phosphate, etc.

In one embodiment, the therapeutic agents employed have a particle size of less than about 10 μm, preferably less than 5 μm.

The use of insufflation powders can represent a preferred embodiment of the present invention and there is provided by the present invention a pharmaceutical product comprising (i) azelastine, or a pharmaceutically acceptable salt, solvate or physiologically functional derivative thereof, provided as an insufflation powder, and (ii) at least one steroid, or a pharmaceutically acceptable salt, solvate or physiologically functional derivative thereof, provided as an insufflation powder, as a combined preparation for simultaneous, separate or sequential use in the treatment of conditions for which administration of one or more anti-histamine and/or one or more steroid is indicated.

It will be appreciated from the above, that the respective therapeutic agents of the combined preparation can be administered simultaneously, either in the same or different insufflation powder formulations, or separately or sequentially. If there is separate or sequential administration as discussed above, it will also be appreciated that the subsequently administered therapeutic agents should be administered to a patient within a time scale so as to achieve, or more particularly optimise, the above referred to advantageous synergistic therapeutic effect of a combined preparation as present in a pharmaceutical product according to the present invention.

The present invention also provides an insufflation powder formulation comprising (i) azelastine, or a pharmaceutically acceptable salt, solvate or physiologically functional derivative thereof, and (ii) at least one steroid, or a pharmaceutically acceptable salt, solvate or physiologically functional derivative thereof, together with a pharmaceutically acceptable carrier or excipient therefor.

Dry insufflation powder formulations as provided by the present invention can be beneficial where it is required that therapeutic agents as employed according to the present invention are retained in the nasal cavity, and systemic side effects can be minimised or eliminated. Furthermore, insufflation powder formulations as employed in the present invention can be beneficial whereby retention of azelastine, or a pharmaceutically acceptable salt, solvate or physiologically functional derivative thereof, at the nasal mucosa is improved, and the bitter aftertaste associated with liquid anti-histamine formulations significantly reduced, whilst also exhibiting the synergistic therapeutic effect associated with the azelastine/steroid combinations provided by the present invention. By providing a dry insufflation powder formulation of azelastine, together with a steroid, having an average particle size of less than about 10 μm, the therapeutic agents can be restricted primarily to the desired target organ, the nasal mucosa.

A dry powder insufflation formulation according to the present invention can be administered by the use of an insufflator, which can produce a finely divided cloud of the dry powder. The insufflator preferably is provided with means to ensure administration of a substantially pre-determined amount of a formulation or product as provided by the present invention. The powder may be used directly with an insufflator which is provided with a bottle or container for the powder, or the powder may be filled into a capsule or cartridge, such as a gelatin capsule, or other single dose device adapted for administration. The insufflator preferably has means to open the capsule or other dose device.

Preferred combinations of therapeutic agents employed in pharmaceutical products and formulations according to the present invention (in particular nasal sprays or drops, aerosol or insufflation products and formulations as described above) comprise any one of the following combinations.

The present invention further provides, therefore, a pharmaceutical product comprising (i) azelastine, or a pharmaceutically acceptable salt thereof, and (ii) at least one steroid selected from the group consisting of beclomethasone, fluticasone, mometasone and pharmaceutically acceptable esters thereof, as a combined preparation for simultaneous, separate or sequential use in the treatment of conditions for which administration of one or more anti-histamine and/or one or more steroid is indicated. Suitably the esters can be selected from beclomethasone dipropionate, fluticasone propionate, fluticasone valerate, mometasone furoate and mometasone furoate monohydrate.

The present invention also provides a pharmaceutical formulation comprising (i) azelastine, or a pharmaceutically acceptable salt thereof, and (ii) at least one steroid selected from the group consisting of beclomethasone, fluticasone, mometasone and pharmaceutically acceptable esters thereof, together with a pharmaceutically acceptable carrier or excipient therefor. Suitably the esters can be selected from beclomethasone dipropionate, fluticasone propionate, fluticasone valerate, mometasone furoate and mometasone furoate monohydrate.

In the case of a nasal spray, a particularly preferred formulation as provided by the present invention is a nasal spray comprising azelastine, or a pharmaceutically acceptable salt thereof (preferably azelastine hydrochloride), together with mometasone either as the free base or in ester form, preferably as mometasone furoate.

Specific combinations of therapeutic agents employed in pharmaceutical products and formulations according to the present invention comprise any one of the following combinations:

azelastine hydrochloride and beclomethasone dipropionate;
azelastine hydrochloride and fluticasone propionate;
azelastine hydrochloride and fluticasone valerate;
azelastine hydrochloride and mometasone furoate; and
azelastine hydrochloride and mometasone furoate monohydrate.

There is also provided by the present invention a method for the prophylaxis or treatment in a mammal, such as a human, of conditions for which administration of one or more anti-histamine and/or one or more steroid is indicated, which method comprises administration of a therapeutically effective amount of a pharmaceutical product substantially as hereinbefore described, as a combined preparation for simultaneous, separate or sequential use in the treatment of such conditions.

The present invention also provides a method for the prophylaxis or treatment in a mammal, such as a human, of conditions for which administration of one or more anti-histamine and/or one or more steroid is indicated, which method comprises administration of a therapeutically effective amount of a pharmaceutical formulation substantially as hereinbefore described.

There is also provided by the present invention for use in the manufacture of a medicament for the prophylaxis or treatment in a mammal, such as a human, of conditions for which administration of one or more anti-histamine and/or one or more steroid is indicated, a pharmaceutical product, as a combined preparation for simultaneous, separate or sequential use in the treatment of such conditions.

There is further provided by the present invention, therefore, a process of preparing a pharmaceutical product substantially as hereinbefore described, which process comprises providing as a combined preparation for simultaneous, separate or sequential use in the treatment of conditions for which administration of one or more anti-histamine and/or one or more steroid is indicated: (i) azelastine, or a pharmaceutically acceptable salt, solvate or physiologically functional derivative thereof, and (ii) at least one steroid, or a pharmaceutically acceptable salt, solvate or physiologically functional derivative thereof.

The present invention also provides a process of preparing a pharmaceutical formulation substantially as hereinbefore described, which process comprises admixing a pharmaceutically acceptable carrier or excipient with: (i) azelastine, or a pharmaceutically acceptable salt, solvate or physiologically functional derivative thereof, and (ii) at least one steroid, or a pharmaceutically acceptable salt, solvate or physiologically functional derivative thereof. Preferably pharmaceutical formulations according to the present invention can comprise insufflation powder formulations, nasal sprays, nasal inhalation solutions or aerosols substantially as hereinbefore described.

The present invention is now illustrated by the following Examples, which do not limit the scope of the invention in any way. In Examples where only the ingredients of formulations according to the present invention are listed, these formulations are prepared by techniques well known in the art.

EXAMPLE 1

| Nasal spray or nasal drops with 0.1% azelastine hydrochloride as active ingredient and steroid 0.1% | | |
|---|---|---|
| Sr. No | Ingredients | Quantity % w/v |
| 1. | Azelastine hydrochloride | 0.1% |
| 2. | Steroid | 0.1% |
| 3. | Disodium edetate | 0.005% |
| 4. | Sodium chloride | 0.9% |
| 5. | Benzalkonium chloride | 0.001% |
| 6. | Avicel RC 591 | 1.2% |
| 7. | Citric acid monohydrate | 0.2% |
| 8. | Disodium hydrogen phosphate dodecahydrate | 0.1% |
| 9. | Purified water | |

EXAMPLE 2

Dosage aerosol giving off 0.5 mg of azelastine hydrochloride and 50 micrograms of beclomethasone dipropionate freon solvate per stroke.

About 8.0 kg of a mixture of 70 parts by weight of difluorodichloromethane and 30 parts by weight of 1,2dichlorotetrafluoroethane are cooled to about −55 degree C. in an appropriate cooling vessel. A mixture of 0.086 kg of pre-cooled sorbitantrioleate and 0.8600 kg of pre-cooled trichlorofluoromethane are dissolved with stirring into the mixture at −55 degrees C., 0.0688 kg of micronized azelastine hydrochloride, 0.00688 kg of beclomethasone dipropionate freon solvate and 0.0688 kg of micronized lactose are then incorporated in portions into the solution thereby obtained with intensive stirring. The total weight of the suspension thereby obtained is made up to 9.547 kg through addition of more of the mixture of 70 parts by weight of difluorodichloromethane and 30 parts by weight of 1,2-dichlorotetrafluoroethane cooled to about −55 degree C.

Following closure of the cooling vessel the suspension is again cooled to about −55 degrees C. under intensive stirring. It is then ready to be filled.

EXAMPLE 3

Nasal spray or nasal drops with Azelastine and steroid*

| Sr. No. | Ingredients | Quantity (% w/w) |
|---|---|---|
| | Azelastine Hydrochloride | 0.10 |
| | Fluticasone propionate | 0.0357 |
| | Glycerin | 2.60 |
| | Avicel RC 591 | 1.35 |
| | Polysorbate 80 | 0.025 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone propionate (50 mcg).

EXAMPLE 4

Nasal spray or nasal drops with Azelastine and steroid*

| Sr. No. | Ingredients | Quantity (% w/w) |
|---|---|---|
| | Azelastine Hydrochloride | 0.10 |
| | Fluticasone valerate | 0.0357 |
| | Glycerin | 2.60 |
| | Avicel RC 591 | 1.20 |
| | Polysorbate 80 | 0.030 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone valerate (50 mcg).

EXAMPLE 5

Nasal spray or nasal drops with Azelastine and steroid*

| Sr. No. | Ingredients | Quantity (% w/w) |
|---|---|---|
| | Azelastine Hydrochloride | 0.10 |
| | Fluticasone propionate | 0.0714 |
| | Glycerin | 2.60 |
| | Avicel RC 581 | 1.35 |
| | Polysorbate 80 | 0.025 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone propionate (50 mcg).

EXAMPLE 6

Nasal spray or nasal drops with Azelastine and steroid

| Sr. No. | Ingredients | Quantity (% w/w) |
|---|---|---|
| | Azelastine Hydrochloride | 0.10 |
| | Mometasone Furoate | 0.05173 |
| | Glycerin | 2.30 |
| | Disodium edetate | 0.005 |
| | Polysorbate 80 | 0.0125 |
| | Avicel RC 581 | 1.35 |
| | Benzalkonium chloride | 0.01 |
| | Citric acid monohydrate | 0.20 |
| | Disodium hydrogen phosphate dodecahydrate | 0.10 |
| | Purified water | q.s. |

EXAMPLE 7

Nasal spray or nasal drops with Azelastine and steroid*

| Sr. No. | Ingredients | Quantity (% w/w) |
|---|---|---|
| | Azelastine Hydrochloride | 0.10 |
| | Mometasone Furoate monohydrate | 0.05173 |
| | Glycerin | 2.60 |
| | Avicel CL 611 | 2.295 |
| | Polysorbate 80 | 0.0125 |
| | Benzalkonium chloride | 0.01 |
| | Phenyl ethyl alcohol | 0.25 |
| | Purified water | q.s. |

*Each spray delivers Azelastine Hydrochloride (140 mcg) and Mometasone furoate (50 mcg).

EXAMPLE 8

Nasal MDI with Azelastine and steroid

| Sr. No. | Ingredients | Quantity in mcg |
|---|---|---|
| | Azelastine Hydrochloride | 140 |
| | Mometasone Furoate monohydrate | 50 |
| | HFA 134a | q.s. |
| | Lecithin | 0.1% |
| | Alcohol | (up to 5%) |

EXAMPLE 9

Nasal MDI with Azelastine and steroid

| Sr. No. | Ingredients | Quantity in mcg |
|---|---|---|
| | Azelastine Hydrochloride | 140 |
| | Fluticasone propionate | 50 |
| | HFA 134a | q.s. |
| | Sorbitan trioleate | 0.1% |
| | Alcohol | (up to 5%) |

EXAMPLE 10

| Nasal MDI with Azelastine and steroid | | |
|---|---|---|
| Sr. No. | Ingredients | Quantity in mcg |
| | Azelastine Hydrochloride | 140 |
| | Fluticasone propionate | 100 |
| | HFA 134a | q.s. |
| | Oleic acid | 0.1% |

EXAMPLE 11

| Nasal MDI with Azelastine and steroid | | |
|---|---|---|
| Sr. No. | Ingredients | Quantity in mcg |
| | Azelastine Hydrochloride | 140 |
| | Fluticasone Valerate | 50 |
| | HFA 134a | q.s. |
| | Alcohol | (up to 5%) |

Insufflatable powders containing Azelastine and Steroid:

EXAMPLE 12

| Sr. No. | Ingredients | Quantity (% w/w) |
|---|---|---|
| | Azelastine Hydrochloride (Micronized) | 140 mcg |
| | Fluticasone propionate | 50 mcg |
| | Lactose | q.s. (up to 25 mcg) |

EXAMPLE 13

| Sr. No. | Ingredients | Quantity (% w/w) |
|---|---|---|
| | Azelastine Hydrochloride (Micronized) | 140 mcg |
| | Fluticasone propionate | 100 mcg |
| | Mannitol | q.s. (up to 30 mcg) |

EXAMPLE 14

| Sr. No. | Ingredients | Quantity (% w/w) |
|---|---|---|
| | Azelastine Hydrochloride (Micronized) | 140 mcg |
| | Fluticasone propionate | 250 mcg |
| | Lactose | q.s. (up to 30 mcg) |

What is claimed is:

1. A method for the prophylaxis or treatment of rhinitis or conjunctivitis in a mammal, comprising intranasal administration to said mammal of a therapeutically effective amount of a pharmaceutical composition comprising (a) azelastine, or a pharmaceutically acceptable salt thereof; and (b) and ciclesonide, or a pharmaceutically acceptable salt or ester thereof.

2. The method of claim 1, wherein the pharmaceutical composition comprises a dosage form suitable for nasal administration.

3. The method of claim 2, wherein the dosage form suitable for nasal administration is in the form of an aerosol, an ointment, nasal drops, or a nasal spray or an inhalation solution.

4. The method of claim 2, wherein the pharmaceutical composition is in the form of a nasal spray.

5. The method of claim 2, wherein the pharmaceutical composition is in the form of nasal drops.

6. The method of claim 1, wherein the pharmaceutical composition is in the form of an aqueous suspension or solution.

7. The method of claim 1, wherein the pharmaceutical composition has a particle size of less than 10 μm.

8. The method of claim 1, wherein the pharmaceutically acceptable salt of azelastine is azelastine hydrochloride.

9. The method of claim 1, wherein the pharmaceutical composition further comprises at least one additive selected from the group consisting of a surfactant, an isotonic agent, a buffer, a preservative, and a suspending agent or a thickening agent, and combinations thereof.

10. The method of claim 9, wherein the surfactant is selected from the group consisting of a polysorbate surfactant, a poloxamer surfactant, and combinations thereof.

11. The method of claim 9, wherein the isotonic agent is selected from the group consisting of sodium chloride, saccharose, glucose, glycerine, sorbitol, 1,2-propylene glycol, and combinations thereof.

12. The method of claim 9, wherein the buffer comprises a citric acid-citrate buffer.

13. The method of claim 9, wherein the preservative is selected from the group consisting of edetic acid and its alkali salts, lower alkyl p-hydroxybenzoates, chlorhexidine, phenyl mercury borate, benzoic acid or a salt thereof, a quaternary ammonium compound, sorbic acid or a salt thereof, and combinations thereof.

14. The method of claim 9, wherein the suspending agent or thickening agent is selected from the group consisting of cellulose derivatives, gelatin, polyvinylpyrrolidone, tragacanth, ethoxose, alginic acid, polyvinyl alcohol, polyacrylic acid, pectin, and combinations thereof.

15. The method of claim 9, wherein the buffer, when present, maintains the pH of the aqueous phase at from 3 to 7.

16. The method of claim 1, wherein the mammal is a human.

17. The method of claim 1, wherein the method is prophylaxis or treatment of allergic rhinitis.

18. The method of claim 1, wherein the method is prophylaxis or treatment of allergic conjunctivitis.

19. The method of claim 1, wherein the pharmaceutical composition is formulated for use as a nasal spray or nasal drops in the treatment of seasonal allergic rhinitis or perennial allergic rhinitis.

20. The method of claim 1, wherein the pharmaceutical composition is formulated for use as nasal spray or nasal drops in the treatment of seasonal allergic conjunctivitis or perennial allergic conjunctivitis.

21. The method of claim 8, wherein the pharmaceutical composition is formulated for use as a nasal spray or nasal drops in the treatment of seasonal allergic rhinitis or perennial allergic rhinitis.

22. The method of claim 8, wherein the pharmaceutical composition is formulated for use as nasal spray or nasal drops in the treatment of seasonal allergic conjunctivitis or perennial allergic conjunctivitis.

23. The method of claim 1, wherein the method is prophylaxis or treatment of seasonal allergic rhinitis.

24. The method of claim 1, wherein the method is prophylaxis or treatment of perennial allergic rhinitis.

25. The method of claim 1, wherein the method is prophylaxis or treatment of seasonal allergic conjunctivitis, 26. The method of claim 1, wherein the method is prophylaxis or treatment of perennial allergic conjunctivitis.

* * * * *

UNITED STATES PATENT AND TRADEMARK OFFICE
CERTIFICATE OF CORRECTION

PATENT NO.        : 8,933,060 B2  
APPLICATION NO.   : 13/644126  
DATED             : January 13, 2015  
INVENTOR(S)       : Amar Lulla and Geena Malhotra Page 1 of 1

It is certified that error appears in the above-identified patent and that said Letters Patent is hereby corrected as shown below:

Title page, Item 71, replace the name of the Applicant "Cipla House" with --Cipla Limited--.

Signed and Sealed this
Twenty-first Day of April, 2015

Michelle K. Lee
*Director of the United States Patent and Trademark Office*

UNITED STATES PATENT AND TRADEMARK OFFICE
CERTIFICATE OF CORRECTION

PATENT NO.         : 8,933,060 B2                               Page 1 of 1
APPLICATION NO.    : 13/644126
DATED              : January 13, 2015
INVENTOR(S)        : Amar Lulla and Geena Malhotra It is certified that error appears in the above-identified patent and that said Letters Patent is hereby corrected as shown below:

In the claims:

• Claim 1, Column 11, Lines 65-66, replace "thereof; and (b) and ciclesonide" with --thereof; and (b) ciclesonide--.

• Claim 3, Column 12, Line 6, replace "drops, or a nasal spray" with --drops, a nasal spray--.

• Claim 20, Column 12, Line 57, replace "as nasal spray" with --as a nasal spray--.

• Claim 22, Column 12, Line 65, replace "as nasal spray" with --as a nasal spray--.

Signed and Sealed this
Twenty-fifth Day of August, 2015

Michelle K. Lee
*Director of the United States Patent and Trademark Office*